US012082971B2

(12) United States Patent
 Capri et al.

(10) Patent No.: US 12,082,971 B2
(45) Date of Patent: Sep. 10, 2024

(54) METHOD FOR SCANNING MATERIAL USING AN ULTRASONIC IMAGING PROBE

(71) Applicant: TROPHY SAS, Marne la Vallee (FR)

(72) Inventors: Arnaud Capri, Marne la Vallee (FR); David Roudergues, Marne la Vallee (FR); Jean-Marc Inglese, Bussy-Saint-Georges (FR); Herve Josso, Marne la Vallee (FR)

( * ) Notice: Subject to any disclaimer, the term of this patent is extended or adjusted under 35 U.S.C. 154(b) by 65 days.

(21) Appl. No.: 17/423,497

(22) PCT Filed: Jan. 16, 2020

(86) PCT No.: PCT/EP2020/051061
§ 371 (c)(1),
(2) Date: Jul. 16, 2021

(87) PCT Pub. No.: WO2020/148405
PCT Pub. Date: Jul. 23, 2020

(65) Prior Publication Data
US 2022/0110606 A1   Apr. 14, 2022

Related U.S. Application Data

(60) Provisional application No. 62/793,357, filed on Jan. 16, 2019.

(51) Int. Cl.
| A61B 8/12 | (2006.01) |
|---|---|
| A61B 8/00 | (2006.01) |
| A61B 8/08 | (2006.01) |
| A61B 8/14 | (2006.01) |
| A61C 19/04 | (2006.01) |

(52) U.S. Cl.
CPC .............. *A61B 8/12* (2013.01); *A61B 8/08* (2013.01); *A61B 8/0875* (2013.01); *A61B 8/14* (2013.01); *A61B 8/4254* (2013.01); *A61B 8/429* (2013.01); *A61B 8/4455* (2013.01); *A61B 8/4466* (2013.01); *A61B 8/4477* (2013.01); *A61B 8/4494* (2013.01); *A61B 8/469* (2013.01);
(Continued)

(58) Field of Classification Search
None
See application file for complete search history.

(56) References Cited

U.S. PATENT DOCUMENTS 10,799,210 B1 * 10/2020 Zhang ................ A61C 9/0086
2006/0270935 A1 * 11/2006 Ariff ..................... A61C 19/04
                                                                600/437
(Continued)

FOREIGN PATENT DOCUMENTS

WO    WO-2018149948 A1 *  8/2018  ............ A61B 8/085

*Primary Examiner* — Joel Lamprecht
*Assistant Examiner* — Ashish S Jasani

(57) ABSTRACT

At least one embodiment of a method for scanning material using a dental ultrasonic imaging probe comprising an ultrasonic device configured for emitting ultrasound signals within at least two emitting cones and for receiving corresponding echoed ultrasound signals, the at least two emitting cones extending in different directions, the method comprising: receiving an item of information relating to a direction for emitting an ultrasound signal; selecting one of the received corresponding echoed ultrasound signals or the ultrasound signals to be emitted as a function of the received item of information.

14 Claims, 6 Drawing Sheets

(52) U.S. Cl.
CPC .............. *A61B 8/5207* (2013.01); *A61B 8/54* (2013.01); *A61B 8/585* (2013.01); *A61C 19/043* (2013.01)

(56) References Cited

U.S. PATENT DOCUMENTS

| | | | |
|---|---|---|---|
| 2010/0227295 A1* | 9/2010 | Maev | A61B 8/0875 |
| | | | 433/215 |
| 2012/0244489 A1* | 9/2012 | Carnahan | A61B 8/0875 |
| | | | 433/25 |
| 2013/0060144 A1* | 3/2013 | Culjat | A61B 8/14 |
| | | | 600/459 |
| 2017/0119505 A1* | 5/2017 | Mörmann | A61B 1/24 |

\* cited by examiner

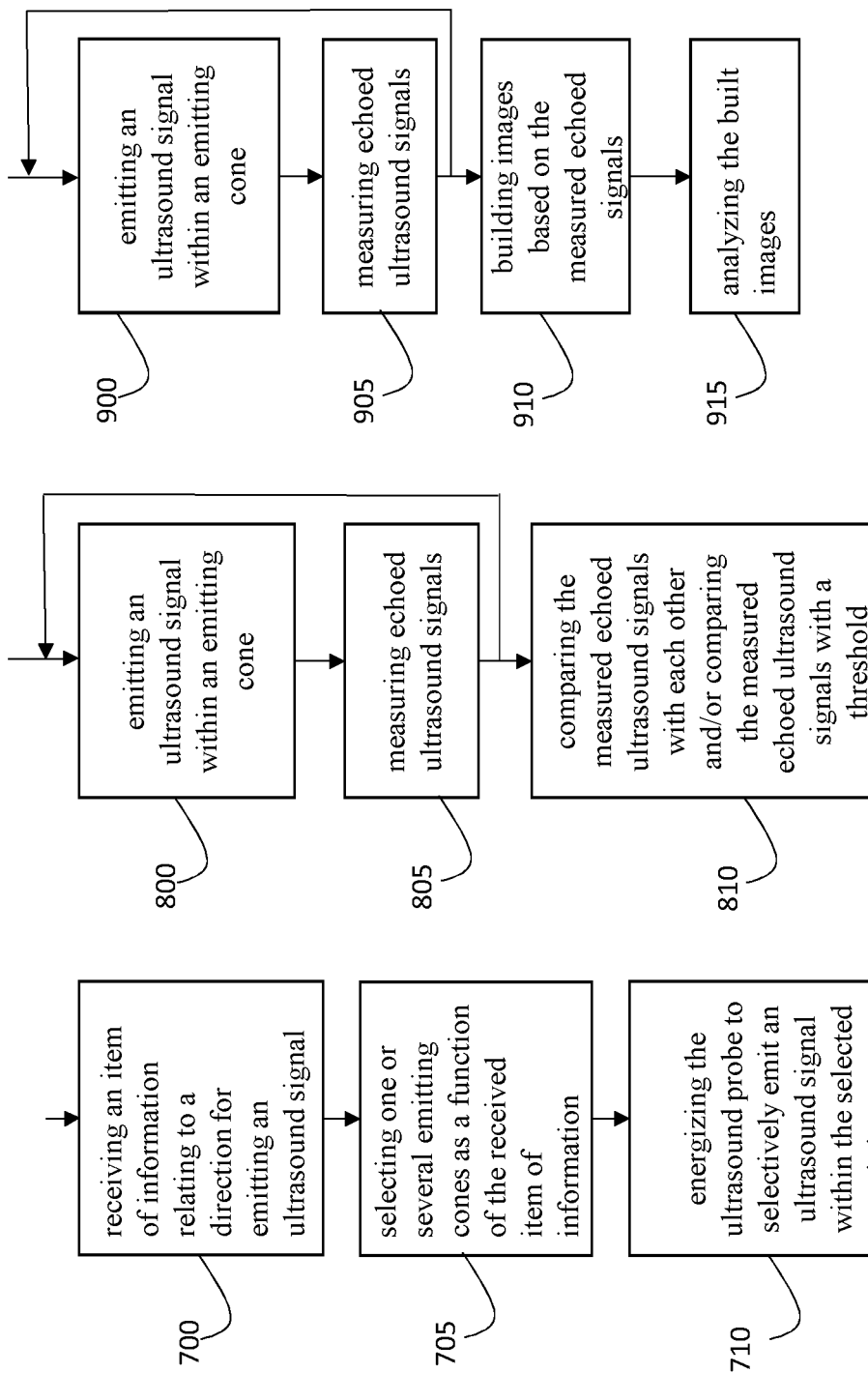

METHOD FOR SCANNING MATERIAL USING AN ULTRASONIC IMAGING PROBE

FIELD OF THE INVENTION

The present invention relates to the technical field of ultrasonic imaging probes and of ultrasonic dental probes for soft tissue imaging.

BACKGROUND OF THE INVENTION

Ultrasound imaging has been adapted for intraoral use in a number of implementations and has been found to have particular utility compared to other conventional methods. Conditions such as gingivitis, for example, can be detected by sensing the acoustic response of tissues. Ultrasound may also provide accurate information about the pathological nature of lesions.

Because of the non-emission of ionizing radiation, ultrasound imaging is inherently safer than ionizing methods and allows the repeatability of the examination if needed. Ultrasound imaging can be used as a substitute for, or a complement to, various types of radiography (cone beam computed tomography or CBCT, panoramic x-ray, or intraoral x-ray imaging), magnetic resonance imaging (MRI), or nuclear medicine.

Ultrasound imaging may use high-frequency sound waves, typically between 1 to 100 MHz. High frequency waves being more attenuated than low frequency waves for a given distance, high frequency waves are suitable mainly for imaging superficial structures, e.g. for dermatology, or dental imaging. Conversely, low frequency waves are suitable for imaging the deepest structures of the body.

An ultrasound imaging apparatus generally comprises one or several transducers that act as ultrasound beam emitters and/or ultrasound beam receivers to receive echoes from the emitted signals. In addition, the ultrasound imaging apparatus may comprise various processing and display components used for generating and presenting images from acquired signals. An ultrasound beam emitter generates an ultrasound signal from an electrical signal and conversely, an ultrasound receiver generates electrical pulses from a mechanical ultrasound signal.

Objects in the path of emitted ultrasound signals return a portion of the ultrasound energy back to the transducer which generates electrical signals indicative of the detected structures. The electrical signals generated from the received ultrasound signal can be delayed for selected times specific to each transducer, so that ultrasonic energy scattered from selected regions adds coherently, while ultrasonic energy from other regions has no perceptible impact. Further, the emission of ultrasound signals can be delayed in order to enable adaptive focusing. The electronic adaptive focusing makes it possible to increase the resolution depending on the depth of the imaged organ.

Array processing techniques used for generating and processing received signals in this way are termed "beamforming".

Particular challenges with intraoral ultrasound imaging relate to the design of a probe that can be used for imaging a full set of intraoral structures, i.e. during periodontal examination, for positioning an ultrasound fan beam along the vertical axis of each tooth of a mouth on both buccal and lingual faces, without the need for extensive modification, reconfiguration, or changing of probe tips or other components. Indeed, to be efficient, the ultrasound probe window must be facing the regions to be imaged. The acoustic paths between the transducer and the regions to be imaged are ensured via coupling materials such as water-based gel to provide acoustic paths with minimal attenuation.

Therefore, there is a need for improving apparatus and method for ultrasound imaging of teeth, gums, and other intraoral features.

SUMMARY OF THE INVENTION

The present invention has been devised to address one or more of the foregoing concerns.

In this context, there is provided a method for scanning material using a dental ultrasonic imaging probe comprising an ultrasonic device configured for emitting ultrasound signals within at least two emitting cones and for receiving corresponding echoed ultrasound signals, the at least two emitting cones extending in different directions, the method comprises:
  receiving an item of information relating to a direction for emitting an ultrasound signal;
  selecting received echoed ultrasound signals or ultrasound signals to be emitted as a function of the received item of information.

According to some embodiments, receiving an item of information may comprise:
  emitting an ultrasound signal in each of the at least two directions;
  measuring echoed ultrasound signals; and
  comparing the measured echoed ultrasound signals with each other and/or comparing the measured echoed ultrasound signals with a threshold.

According to some embodiments, receiving an item of information may comprise:
  emitting an ultrasound signal in each of the at least two directions;
  measuring echoed ultrasound signals;
  building images based on the measured echoed signals; and
  analyzing the built images.

According to some embodiments, receiving an item of information may comprise receiving a user input.

According to some embodiments, the user input may result from a predetermined mechanical pressure of the dental ultrasonic imaging probe against an intraoral surface.

According to some embodiments, the user input may result from an actuation of a physical button arranged on the dental ultrasonic imaging probe and/or from choosing an item displayed on a software graphic interface hosted on a computer connected to the dental ultrasonic imaging probe.

According to some embodiments, the user input may result from a predetermined movement of the dental ultrasonic imaging probe.

According to some embodiments, the dental ultrasonic imaging probe may comprise at least an indicator configured to provide an item of information relating to the selected emitting cone or a selected emitting direction, and wherein the method comprises:
  energizing the indicator to indicate the selection.

According to some embodiments, the indicator may comprise a plurality of light emitting devices.

According to some embodiments, after receiving an item of information the method may comprise:
  preselecting several fan beams and/or cones with different widths;
  According to some embodiments, selecting one of the emitting ultrasound signals may comprise:

selecting one of the preselected fan beams and/or cones and/or selecting a subsector of one of the preselected fan beams and/or cones as a function of the measured echoed ultrasound signals.

According to some embodiments, the ultrasound probe may be energized to selectively emit the ultrasound signal according to the item of information.

According to some embodiments, the at least two emitting cones may be obtained from two different transducers, from one moving transducer, or from a fixed transducer associated with a moving deflector.

According to a second aspect of the invention, there is provided a computer program for a programmable apparatus, the computer program comprising a sequence of instructions for implementing each of the steps of the method as described hereinbefore when loaded into and executed by the programmable apparatus.

According to a third aspect of the invention, there is provided a device comprising a microprocessor configured for carrying out each of the steps of the method as described hereinbefore.

BRIEF DESCRIPTION OF THE DRAWINGS

Other features and advantages of the invention will become apparent from the following description of non-limiting exemplary embodiments, with reference to the appended drawings, in which:

FIGS. 7 to 9 are diagrams of examples of the method for scanning material according to particular embodiments of the invention.

DETAILED DESCRIPTION OF EMBODIMENTS OF THE INVENTION

Figure 1A:
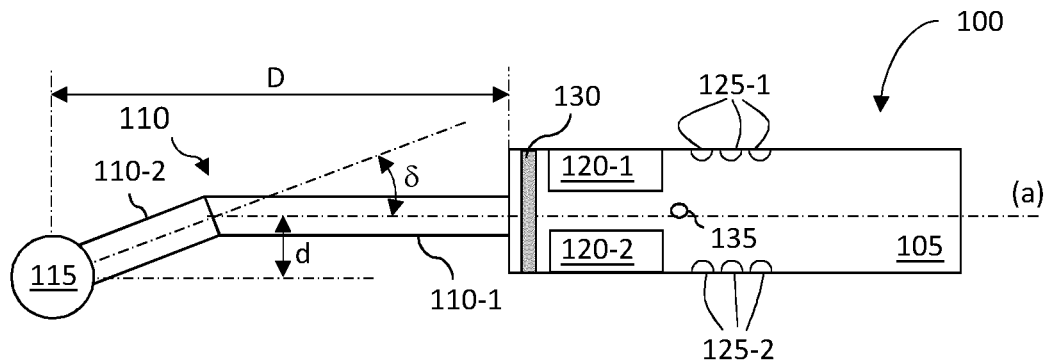
FIGS. 1a to 1c are schematic representations of a rigid ultrasonic imaging probe.

The following is a detailed description of particular embodiments of the invention, reference being made to the drawings in which the same reference numerals identify the same elements of structure in each of the Figures.

In the drawings and text that follow, like components are designated with like reference numerals, and similar descriptions concerning components and an arrangement or interaction of components already described are omitted. Where they are used, the terms "first", "second", and so on, do not necessarily denote any ordinal or priority relation, but may simply be used to more clearly distinguish one element from another, unless specified otherwise.

As used herein, the term "energizable" relates to a device or set of components that perform an indicated function upon receiving power and, optionally, upon receiving an enabling signal.

When referring to the shape of an apparatus, the term "rigid" should be understood as the substantially non-deformable nature of the apparatus, in normal use, which means that the relative position of main elements of the apparatus is substantially constant (i.e. there is no significant shape deformation during use). For example, the relative position of a grip portion, of a support member, and of an ultrasonic device of a rigid ultrasonic imaging probe is substantially constant when the imaging probe is used for imaging intraoral structures. This does not prevent the apparatus from being deformable during a configuration step, for example in a case in which two elements of the apparatus are fastened with a lockable hinge. In addition, this does not prevent the apparatus from comprising slightly deformable parts. For example, the grip portion of a rigid ultrasonic imaging probe may comprise a deformable handgrip such as a handgrip comprising elastic foam.

In the context of the present disclosure, the terms "viewer", "operator", and "user" are considered to be equivalent and refer to the viewing practitioner, technician, or other person who acquires, views, and manipulates an ultrasound image, such as a dental image, on a display monitor. An "operator instruction," "user instruction," or "viewer instruction" is obtained from explicit commands entered by the viewer, such as by clicking a button on the ultrasound probe or system hardware or by using a computer mouse or by using a touch screen or a keyboard entry.

In the context of the present disclosure, the phrase "in signal communication" indicates that two or more devices and/or components are able to communicate with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

The term "subject" refers to the tooth or other portion of a patient that is being imaged and, in optical terms, can be considered equivalent to the "object" of the corresponding imaging system.

Figure 1B:
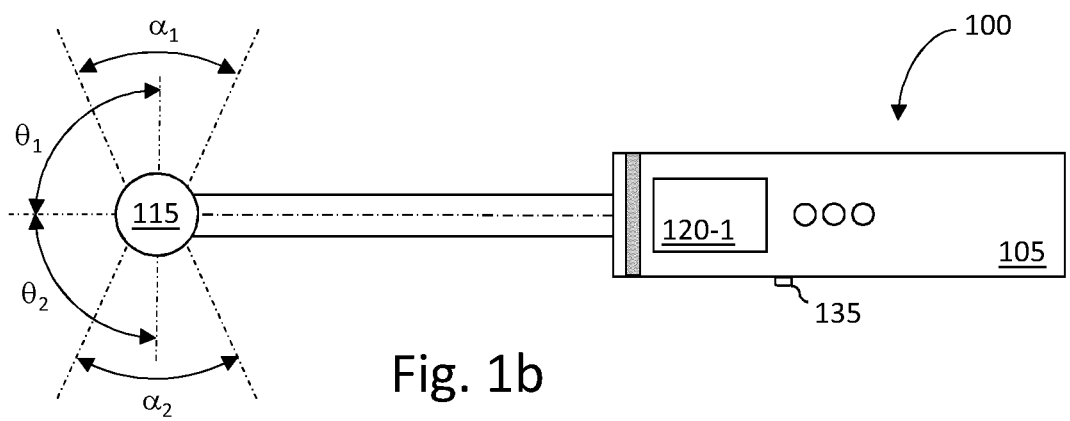
Figure 1C:
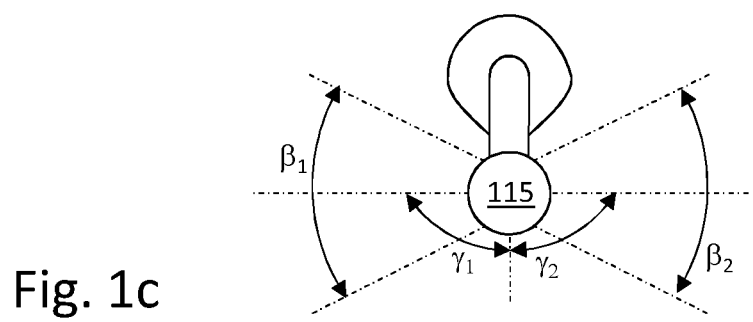

FIGS. 1a and 1b are schematic representations of a rigid ultrasonic imaging probe that may be used in conjunction with particular embodiments of the method of the invention. FIG. 1a is a perspective view of the rigid ultrasonic imaging probe in a measurement configuration while FIGS. 1b and 1c represent a top view and a front view, respectively, of the same rigid ultrasonic imaging probe in the initial configuration. For the sake of the explanation, the initial configuration is distinguished from other measurement configurations, but it is not excluded that measurements are performed with the probe in the initial position.

The probe provides the ultrasound pulse signal emission and/or mechanical components for generating ultrasound beams in an emitting cone. The ultrasound beams may be cone-shaped beams or fan-shaped beams contained in the emitting cone. The cone-shaped ultrasound beams may correspond to the emitting cone or be smaller than the emitting cone. Fan-shaped beams are planar.

The probe also provides acquisition logic for beamforming functions. A computer (not represented) obtains acquired signal data corresponding to received pulse echoes, processed or not, and renders images of the examined objects on a display (not represented). The image content can also be stored for subsequent use or transmitted to another system or to a data storage apparatus or system.

As illustrated, the ultrasonic imaging probe 100 comprises a grip portion 105, a support member 110, and an ultrasonic device 115 (also referred to as ultrasonic sensor). According to the illustrated example, support member 110 comprises two main parts denoted 110-1 and 110-2, the longitudinal axis of part 110-2 being different from the longitudinal axis of the grip portion 105. It is to be noted that according to other examples, part 110-2 is fastened directly to grip portion 105 (i.e. without using part 110-1). Therefore, according to the illustrated example, ultrasonic device 115 is rigidly fastened to grip portion 105 in such a way that it is offset from the grip portion with regard to its longitudinal axis. As apparent from FIG. 1*a*, ultrasonic device 115 is located at a distance d from the longitudinal axis (a) of grip portion 105. Distance d may be chosen between 0 and 5 centimeters. For the sake of illustration, it may be equal to 2 centimeters. Distance D between ultrasonic device 115 and grip portion 105 may be chosen between 4 and 25 centimeters. For the sake of illustration, it can be equal to 10 centimeters.

According to particular embodiments, support member 110 may comprise two tubular members forming an angle δ between their longitudinal axes, may comprise one or more tubular members and a portion of an annular member, or may comprise any composition of members making it possible to axially offset the ultrasonic device from the grip portion.

As illustrated, grip portion 105 may comprise elements enabling a user to interface with functions of ultrasonic imaging probe 100 and/or with a computer system processing signals acquired by ultrasonic imaging probe 100. Such elements may comprise displays generically referenced 120 (e.g. standard displays or touch screens) and buttons generically referenced 125. According to particular embodiments, all these elements or a subset of these elements may be duplicated (120-1/120-2 and 125-1/125-2) so that a user may interact similarly with ultrasonic imaging probe 100 and/or with a computer system processing signals acquired by ultrasonic imaging probe 100 whatever the position of the ultrasonic imaging probe 100 between a first and a second position (the second position being located on the opposite side of a horizontal plane relative to the first position).

In addition, grip portion 105 may comprise a set of LEDs (acronym of light emitting devices), for example the ring of LEDs 130. As described hereafter, these LEDs may be indicative of a selected emitting cone.

According to some embodiments, the LEDs or the ring of LEDs is arranged on the ultrasonic device or on the support member, close to the ultrasonic sensor.

As illustrated in FIG. 1*b*, ultrasonic device 115 may be configured to make measurements according to two opposite directions, with reference to a vertical plane that is perpendicular to a horizontal plane comprising the longitudinal axis (a) of grip portion 105. Ultrasound fan beams may belong to emitting cones having angular cones $\alpha_1$ and $\alpha_2$ and angular cones $\beta_1$ and $\beta_2$, as illustrated in FIG. 1*b* and FIG. 1*c*, that may be in a range of 20° to 160°. Hereinafter, the expression "emitting cone" relates to the two angular cones constituting the emitting cones as described hereinbefore.

The transducers of the ultrasonic imaging probe 100 may be of the A-mode, B-mode (or 2D mode), C-mode, M-mode, Doppler mode, Color Doppler mode, Continuous Doppler mode, Pulsed wave Doppler mode, Duplex mode, Pulse inversion mode, or Harmonic mode type, each of them being well-known to the one skilled in the art.

It is noted that although the directions of the two emitting cones (i.e. the cones in which ultrasound fan beams may be emitted) represented in FIGS. 1*b* and 1*c* are perpendicular to the longitudinal axis of grip portion 105 and to a vertical plane, these directions may be different. These directions may form angles $\theta_1$ and $\theta_2$ with regard to the longitudinal axis of grip portion 105 and angles $\gamma_1$ and $\gamma_2$ with regard to a vertical axis perpendicular to the longitudinal axis of grip portion 105, respectively, varying from about 20° to 160°, provided that these directions are opposite to each other, respectively, with regard to a plane comprising the longitudinal axis of grip portion 105.

FIGS. 2*a* to 2*d* illustrate examples of use of an ultrasonic imaging probe according to particular embodiments of the invention.

Figure 2A:
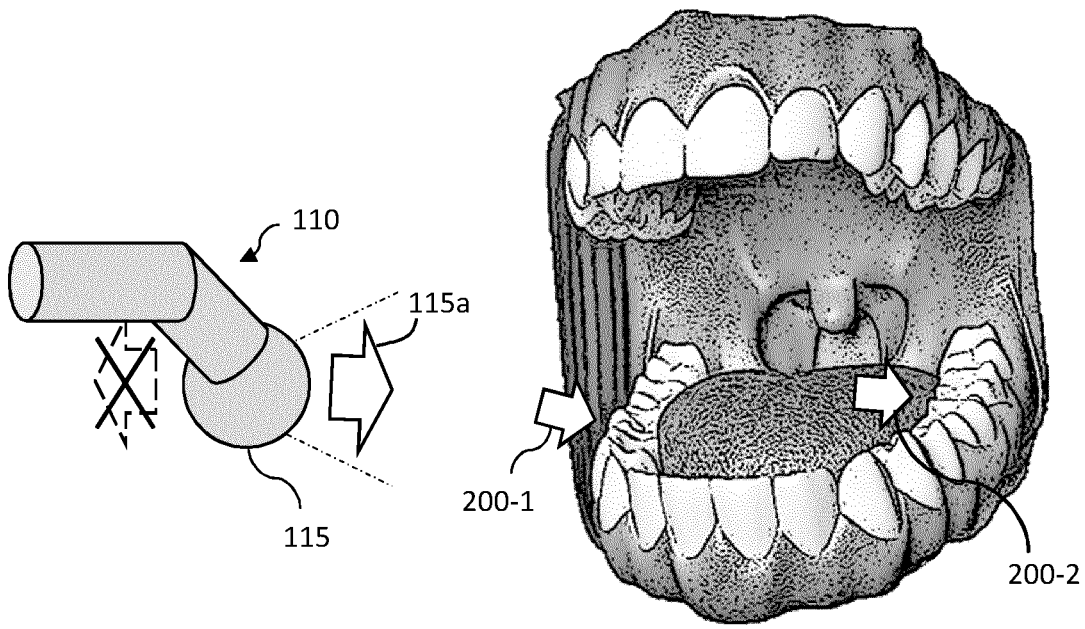
FIGS. 2a to 2d illustrate examples of use of an ultrasonic imaging probe according to particular embodiments of the invention.
Figure 2B:
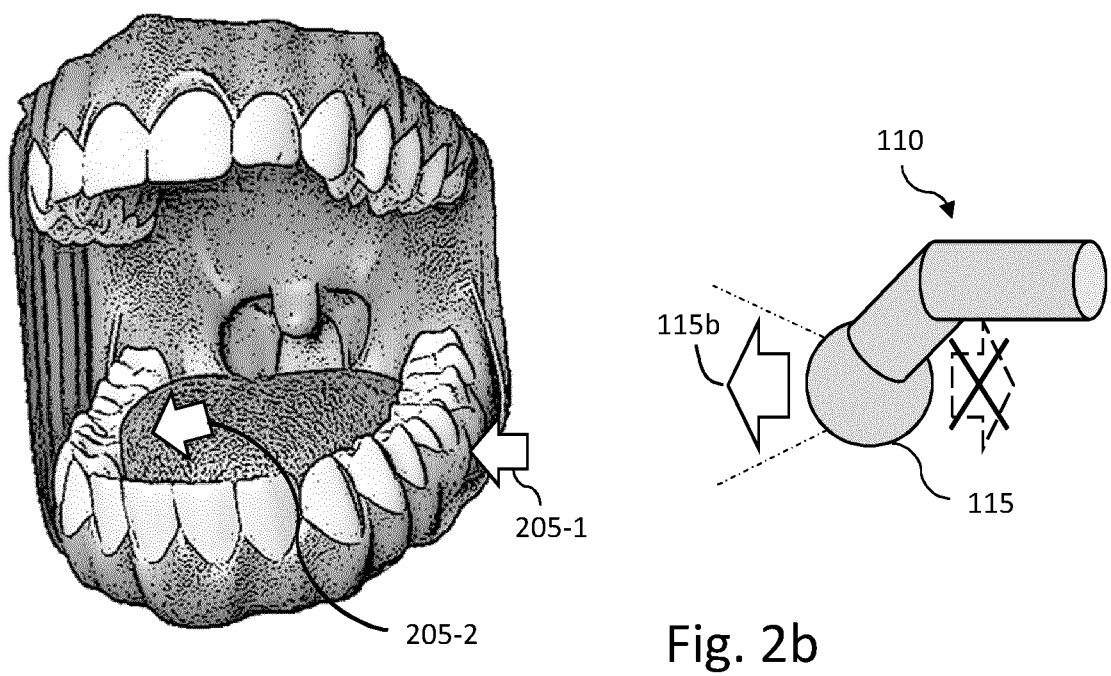
Figure 2C:
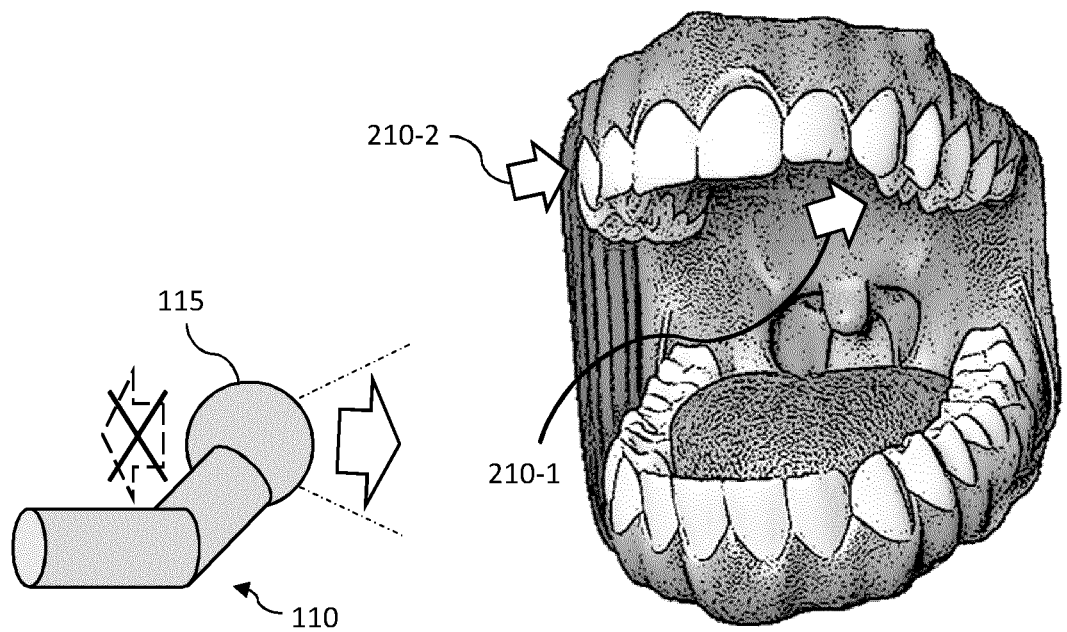
Figure 2D:
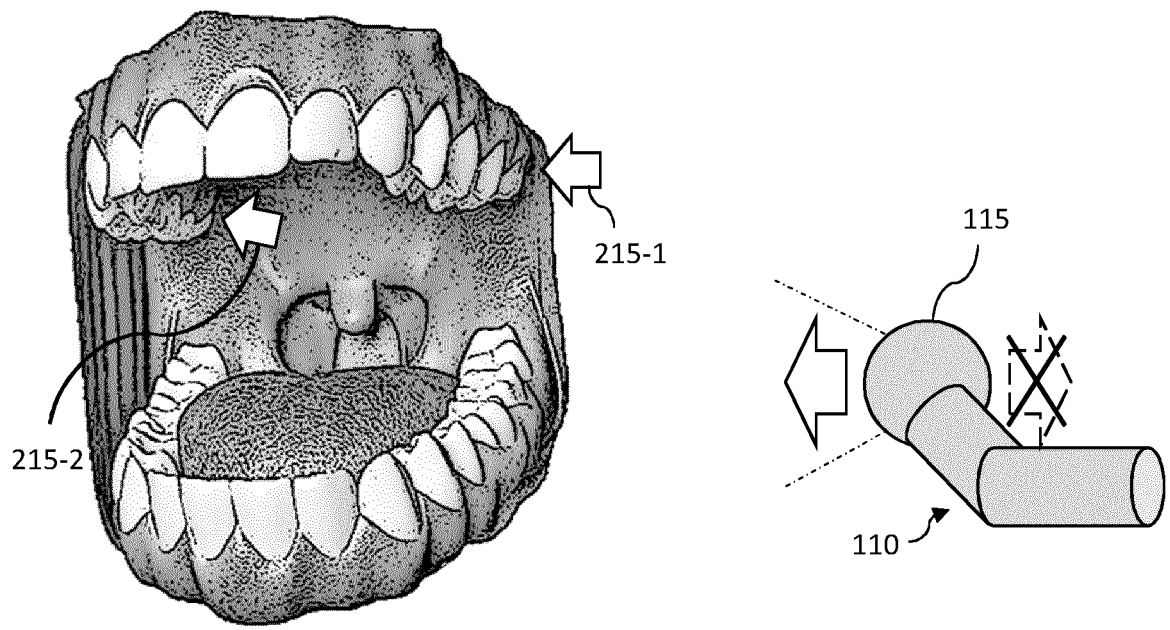

FIGS. 2*a* and 2*b* illustrate two examples of use of ultrasonic imaging probe 100 in a position according to which ultrasonic device 115 is positioned under the grip portion (while considering the horizontal plane comprising the longitudinal axis of the grip portion), while FIGS. 2*c* and 2*d* illustrate two examples of use of ultrasonic imaging probe 100 in a position according to which ultrasonic device 115 is above the grip portion (still considering the horizontal plane comprising the longitudinal axis of the grip portion).

As illustrated in FIGS. 2*a* and 2*c*, measurements are made only on the right side of the probe from the perspective of the operator holding the probe (indicated by arrow 115*a*). For these two measurements the same transducer may be used.

Conversely in FIGS. 2*b* and 2*d*, measurements are made only on the left side of the probe from the perspective of the operator holding the probe (indicated by arrow 115*b*). For these two measurements the same transducer may be used, which may be different from the one used for measurements of FIGS. 2*a* and 2*c*.

Accordingly, by choosing the appropriate orientation of the ultrasonic imaging probe 100 and by making measurements on the appropriate side of ultrasonic device 115, it is possible, using the same ultrasonic imaging probe 100, to make a precise and full examination of the mouth of a patient. The side on which measurements are to be made may be selected by the user, for example using a manual selector (e.g. one of the buttons 125) or may be selected automatically using auto-detection. Auto-detection can be based on factors such as acoustic signal timing or on image features such as distribution of image values or image quality.

Therefore, ultrasonic imaging probe 100 can be used to examine each portion of the jaw (enumerated examples hereinafter are from the perspective of the patient):

left lingual of the mandible, reference 200-2 in FIG. 2*a*,
right buccal of the mandible, reference 200-1 in FIG. 2*a*,
left buccal of the mandible, reference 205-1 in FIG. 2*b*,
right lingual of the mandible, reference 205-2 in FIG. 2*b*,
left lingual of the maxilla, reference 210-1 in FIG. 2*c*,
right buccal of the maxilla, reference 210-2 in FIG. 2*c*,
left buccal of the maxilla, reference 215-1 in FIG. 2*d*, and
right lingual of the maxilla, reference 215-2 in FIG. 2*d*.

According to some embodiments, support member 110 can be deformed so as to make it possible to modify the distance between the ultrasonic device and the main axis of the grip portion, for example to adapt the ultrasonic imaging probe 100 to different types and/or sizes of dental arches. This can result from using elastic materials and/or from using two or more sub-members that are fastened to each other using fastening means enabling the relative position of these sub-members to be changed. The fastening means advantageously comprise locking means to avoid modifying accidentally the relative position of the sub-members.

Figure 3:
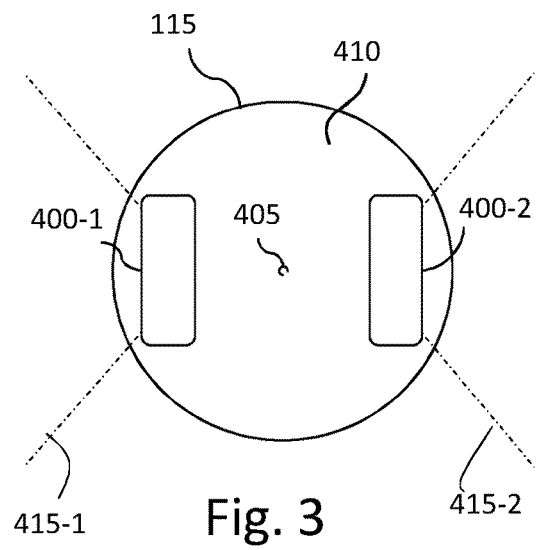
FIGS. 3, 4, 5a, and 5b are sectional views of examples of an ultrasonic sensor of an ultrasonic imaging probe.
Figure 4:
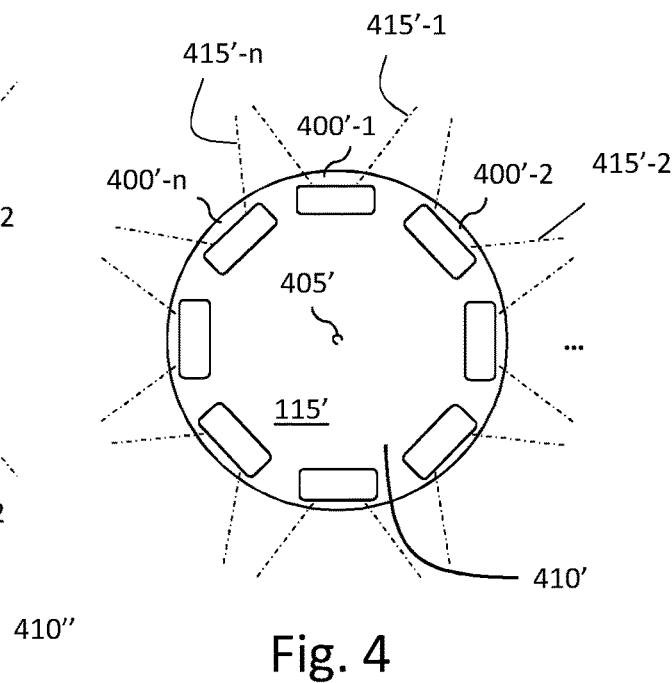

According to particular embodiments, the ultrasonic imaging probe 100 comprises a single transducer with a moving element (e.g. a moving transducer and/or a moving reflector), two or more transducers, or two or more arrays of transducers, arranged around an axis of the ultrasonic device that is parallel to the longitudinal axis of the grip portion, at least on each side of the ultrasonic device (when considering a measurement position of the probe 100), as described by reference to FIGS. 3 to 5.

The transducers can act like an ultrasound beam emitter but also as an ultrasound beam receiver, configured to measure echoed ultrasound. Throughout the rest of the document, the transducers are both ultrasound beam emitters and receivers. In another embodiment, it may be considered that some transducers only act as ultrasound beam emitter or ultrasound beam receiver.

When acting as an emitter, the transducer is associated with an emitting cone that defines the volume in which the associated transducer is able to emit an ultrasound signal.

When acting as a receiver, the transducer is passive and is configured to act as a sensor and to detect and measure any received echoed ultrasound signals. In other words, the transducer detects and measures the incidents waves.

According to some embodiments, each transducer may comprise several emitting elements and/or several receiving elements. Having several receiving elements helps improve ultrasound beam reception while reducing the effect of noise on the received ultrasound signals.

FIG. 3 is a sectional view of a first example of an ultrasonic device that comprises two transducers 400-1, 400-2 (or two arrays of transducers) arranged on each of its sides, rigidly fastened to the ultrasonic sensor. It is a sectional view according to a plane perpendicular to the longitudinal axis of the grip portion 105 when the probe is arranged as illustrated in FIG. 1a As illustrated, ultrasonic device 115 comprises two transducers (or arrays of transducers) 400-1 and 400-2, rigidly fastened to ultrasonic device 115, that are arranged on each side of the longitudinal axis 405 of the device (that is parallel to the longitudinal axis of the grip portion 105 when the probe is arranged as illustrated in FIG. 1a), with regard to a vertical plane. As detailed hereinafter, the transducer or array of transducers that should be used for making measurements can be selected by the user or can be selected automatically.

Each of the two transducers 400-1 and 400-2 respectively defines a cone 415-1 or 415-2, wherein ultrasound beam can be emitted or received by the transducers 400-1 and 400-2. The two transducers 400-1 and 400-2 may be impacted by reflected waves coming from several directions. According to some embodiments, transducers 400-1 and 400-2 are selectively activable so that they can be selectively activated.

FIG. 4 is a sectional view of a second example of an ultrasonic device that comprises a ring of transducers 400'-1 to 400'-n (or of arrays of transducers). Again, it is a sectional view according to a plane perpendicular to the longitudinal axis of the grip portion of the probe 105 when the probe is arranged as illustrated in FIG. 1a.

As illustrated, ultrasonic device 115' comprises a ring of transducers (or of arrays of transducers) 400'-1 to 400'-n, rigidly fastened to ultrasonic device 115', which are arranged around the longitudinal axis 405' of the device (that is parallel to the longitudinal axis of the grip portion 105). According to particular embodiments, one or several neighboring transducers (or arrays of transducers) are used to make measurements at a given time. Again, this can be done by activating only some of them or by processing the signals received from only some of them, the transducers (or arrays of transducers) to be used being selected by the user or automatically.

As represented in FIG. 4, each of the transducers 400'-1 to 400'-n is associated with a cone, referenced 415'-1 to 415'-n, in which the ultrasonic beams referenced 400'-1 to 400'-n are emitted or the echoed ultrasound beams can be detected/received by the considered transducer.

Figure 5A:
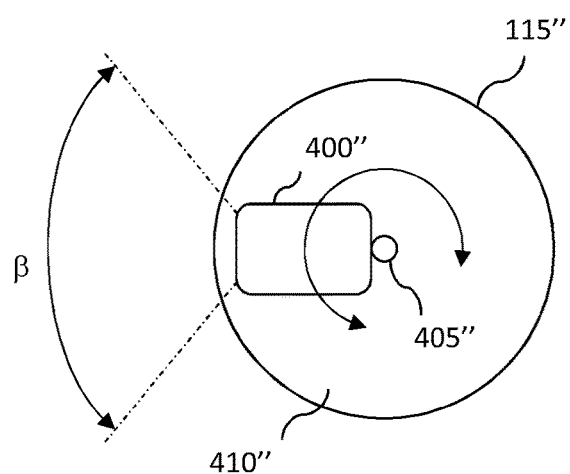

FIG. 5a is a sectional view of a third example of an ultrasonic device which comprises a single transducer (or array of transducers). Again, it is a sectional view according to a plane perpendicular to the longitudinal axis of the grip portion 105 when the probe is arranged as illustrated in FIG. 1a.

As illustrated, the single transducer (or array of transducers) 400" is rotatably mounted within cavity 410" of ultrasonic device 115" so that it can rotate around axis 405", that is parallel to the longitudinal axis of the grip portion. Therefore, the ultrasonic device can emit ultrasound signals according to a given lateral angular cone (denoted β in FIG. 5), that depends on the characteristics of the transducer (or array of transducers), and according to any angular position of the transducer (or array of transducers) over an angular cone that is greater than emitting angular cone β, for example over a full 360° radius.

Figure 5B:
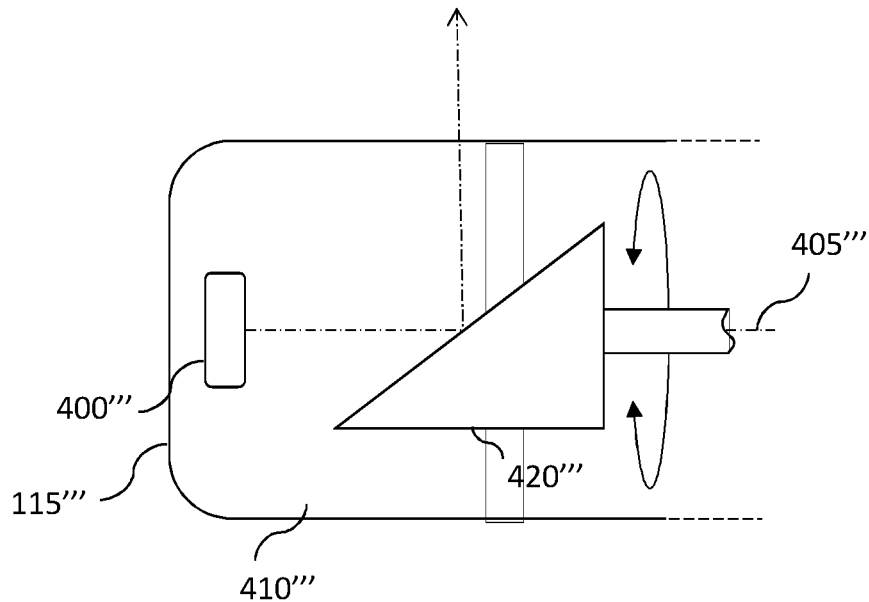

FIG. 5b is a sectional view of a fourth example of an ultrasonic device that comprises a single transducer (or array of transducers). It is a sectional view according to a vertical plane comprising or parallel to the longitudinal axis of the grip portion 105 when the probe is arranged as illustrated in FIG. 1a.

As illustrated, the single transducer (or array of transducers) 400''' is rigidly fastened within the ultrasonic device and a reflective element, or deflector, denoted 420''' is rotatably mounted within cavity 410''' of ultrasonic device 115''', in front of the transducer (or array of transducers) for enabling the latter to emit and/or receive ultrasound signals over a full 360° radius or over a portion of the full 360° radius.

According to the illustrated example, transducer (or array of transducer) 400''' is arranged so as to emit and receive ultrasound signals along a main direction given by axis 405''' that is parallel to the longitudinal axis of the probe. Reflective element 420''' is rotatably mounted in front of the transducer (or array of transducers) for redirecting emitted and/or received ultrasound signals according to lateral angular sectors.

In this case, the fixed transducer 400''' emits an initial emitting cone which is deflected in order to obtain at least two emitting cones extending in two different directions.

The transducer(s) in the several illustrated examples are mounted in a cavity (410, 410', 410" and 410'''). The external surface of each transducer is arranged at a distance of the internal surface of the cavity of the probe tip 115. In order to allow the propagation of soundwave from the transducer to the probe tip 155 surface, the cavity (410, 410', 410" and 410''') is filled with coupling material such as water-based gel to provide acoustic paths with minimal attenuation. Several types of coupling material may be used, for example water (tap water or mineral water), humectant gel (such as the humectant gel known under the trademark Bioxtra, the Sensileave gel from Pierre Fabre, and the humectant gel from Sunstar).

According to some embodiments, the external surface of each transducer is arranged in contact with the internal surface of the cavity of the probe tip. In that case there is no need to fill the cavity with a coupling material.

It is noted here that there exist mechanisms for enabling a transducer or an array of transducers to rotate in an ultrasonic sensor, such as the one described in the document written by Xingying Wang et al., entitled "*Development of a*

Mechanical Scanning Device With High-Frequency Ultrasound Transducer for Ultrasonic Capsule Endoscopy", IEEE Transactions on Medical Imaging, Vol. 36 No. 9, September 2017, pp. 1922-1929.

Thus, ultrasound signals may be emitted according to any given angular position so as to make measurements for angular cones of interest. Echoed ultrasound signals may reach the rotatable transducer configured to detect incident ultrasound waves. To this end, the transducer continuously rotates (emitting only in the given positions and measuring the echoed signals in relation to the transducer's position) or moves when needed to reach a position from which ultrasound signals are to be emitted and/or measured. According to some embodiments, at each reached position, the transducer emits and then possibly measures echoed ultrasound signals.

In such a case, the given angular positions may be defined by settings or by the user or may be dynamically adapted, for example as a result of an analysis of received ultrasound signals.

As described above, in reference to FIGS. 1*a* and 1*b*, the ultrasonic imaging probe 100 may comprise a button, a switch, or a ring of buttons that may take, for example, the form of a rotatable sleeve or collar, for controlling the directions according to which measurements are to be made. A touch-sensitive screen arranged on the ultrasonic imaging probe 100 may also be used to select these directions. The ultrasonic imaging probe 100 may also comprise a sensor for measuring mechanical pressure so that the directions of measurements is set automatically when the user press the probe 100 against the mandible or the maxilla.

Alternatively, ultrasound signals may be emitted and measured from each of 360/β angular positions so that measurements are made for the full 360° radius. In such a case, only meaningful measured signals are preferably processed to render images.

Electronic Elements of the Ultrasonic Imaging Probe

Figure 6:
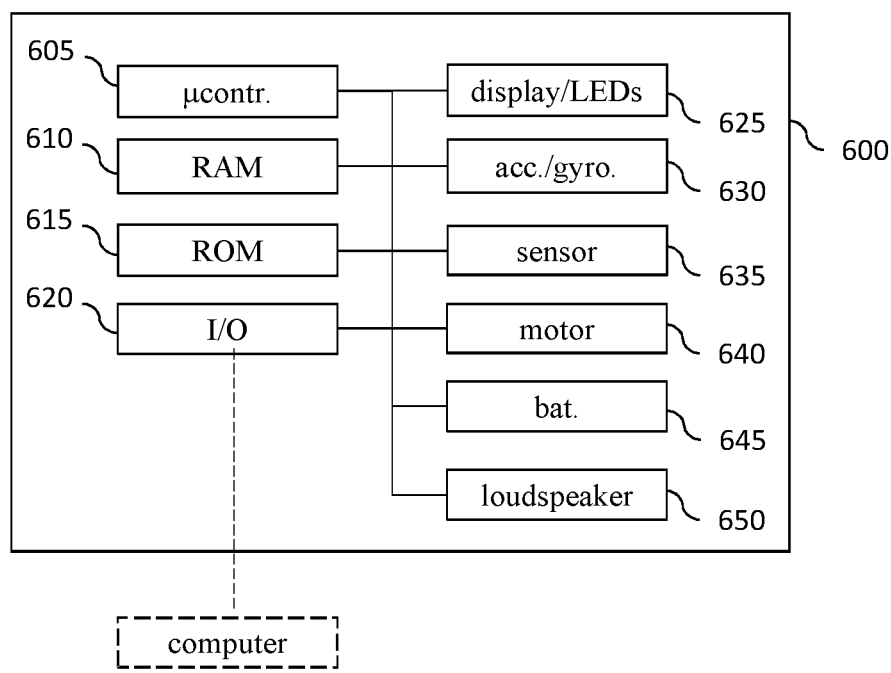
FIG. 6 is a schematic diagram illustrating an example of an electronic system of an ultrasonic imaging probe.

FIG. 6 is a schematic diagram illustrating an example of an electronic system of an ultrasonic imaging probe 100.

As illustrated, the electronic system 600 comprises buses and/or electrical connections connecting:

- a microcontroller 605;
- a random access memory 610, denoted RAM, for storing the executable code for operating the ultrasonic imaging probe 100 as well as the registers adapted to record variables and parameters;
- a read-only memory 615, denoted ROM, for storing computer programs for operating the ultrasonic imaging probe 100 and/or configuration parameters;
- an input/output interface 620 to set the ultrasonic imaging probe 100 in signal communication with a remote computer, for interfacing the ultrasonic imaging probe 100 with the remote computer, for example to transmit measured signals and/or receiving commands for controlling some of the operations of the ultrasonic imaging probe 100, the input/output interface being a wired or wireless interface, for example a wireless interface complying with the WiFi and/or Bluetooth standards (WiFi and Bluetooth are trademarks);
- a display and/or LEDs 625 for giving indications to the user, for example the state of the ultrasonic imaging probe 100, a step or a next step to do, and/or the direction according to which measurements are made or will be made;
- a motion sensor, a position sensor, and/or an orientation sensor 630 comprising, for example, an accelerometer and a gyroscope, making it possible to determine the position, the orientation, the speed, and/or the acceleration of the ultrasonic imaging probe 100, which may be used, for example, to identify commands by gesture type (e.g. a particular gesture may be used to select the directions according to which measurements are to be made);
- an ultrasonic device 635 comprising one or more transducers or arrays of transducers as described above;
- a motor 640 for moving parts of the ultrasonic sensor, for example a transducer, an array of transducers, or a reflecting element;
- a battery 645, rechargeable or not, for providing electrical power to the components of the electronic system; and
- a loudspeaker 650, for giving indications to the user, such as information relating to the state of the probe or performed measurements.

It is to be noted that the ultrasound imaging device may comprise other electronic elements such that some of the electronic components mentioned above may not be required. For example, a motor is not required if the ultrasonic imaging probe 100 comprises several fixed transducers or arrays of transducers. Likewise, internal electrical power may not be required if the ultrasonic imaging probe 100 is connected to a remote computer via wires.

According to some embodiments, the executable code may be stored either in read-only memory 615 or on a removable digital medium such as for example a micro memory card. According to a variant, the executable code of the programs can be received from the remote computer via the input/output interface, in order to be stored in one of the storage means of the communication device 600.

Microcontroller 605 is adapted to control and direct the execution of the instructions or portions of software code of the program or programs for operating the ultrasonic imaging probe 100 according to particular embodiments of the invention, the instructions being stored in one of the aforementioned storage means. After powering on, microcontroller 605 is capable of executing instructions from main RAM memory 610 relating to a software application after those instructions have been loaded from ROM 615 or from a remote computer for example.

Microcontroller 605, RAM 610, and/or ROM 615 may be implemented in hardware by a machine or a dedicated component, such as an FPGA (Field-Programmable Gate Array) or an ASIC (Application-Specific Integrated Circuit).

Upon reception, the acquired ultrasound signals may be processed, for example filtered, by electronic system 600, for example by microcontroller 605, before being transmitted to the remote computer through input/output interface 620. According to particular embodiments, the acquired ultrasound signals may be processed to generate images that are transmitted to the remote computer. Alternatively, the acquired ultrasound signals may be transmitted directly to the remote computer as raw data. The processing power and capabilities of electronic system 600 may depend on the processing to be applied to the acquired ultrasound signals.

The motion sensor and/or orientation sensor may be used to detect predetermined commands. For example, a movement of the ultrasonic imaging probe 100 to the right may indicate that measurements are to be made on the right side of the ultrasonic imaging probe 100. Likewise, a movement of the ultrasonic imaging probe 100 to the left may indicate that measurements are to be made on the left side of the ultrasonic imaging probe 100.

The motion sensor and/or orientation sensor may also be used to determine the position of the ultrasonic imaging probe 100 with regard to a default position. The determined position of the ultrasonic imaging probe 100 may be used to appropriately orient images generated from received ultrasound signals.

As described above, an indication may be displayed on a display or as a subset of one or more LEDs to provide an indication regarding the direction according to which measurements are made. According to some embodiments, piezoelectric elements surrounding the reception area are used to generate energy for energizing local indicators (for example small LEDs) in the vicinity of the probe tip 115.

To that end, piezoelectric elements, such as those used in transducers, having the capability to both generate a mechanical wave due to electrical excitation and, conversely, to generate an electrical pulse once placed under mechanical stress, are used. When using the ultrasonic imaging probe 100, a transducer generates a number of ultrasound waves that are reflected and deviated by the observed tissues. During signal acquisition, for generating images, incident waves not only impact the transducer but also affect areas outside the transducer surface, including portions of the piezoelectric material not used for capturing signals, called piezoelectric wells for the sake of clarity. Therefore, it is possible to use part of the excess energy that is otherwise lost, in the vicinity of the emitters and receivers actually used to make measurements, by considering a number of piezoelectric sources for energy harvesting. These piezoelectric wells can capture excess energy that is not captured as part of the reflected acoustic signal and generate sufficient current to energize small LEDs and associated capacitive elements. As described above, the generated illumination from this energy harvesting can provide information to the user, to visually highlight the position or angular orientation of the emitted ultrasound beam. The generated illumination may even be strong enough to illuminate the scanned area.

According to some embodiments, the probe may be autonomous. In other words, the probe may be usable without any other systems, such as a remote computer. In this case, the probe may be configured to emit ultrasound signals, to acquire echoed ultrasound signals, to build an ultrasound image, to perform measurements and then to display notifications on the LCD display of the ultrasound probe. Consequently, the probe may comprise a microcontroller associated to memory (such as RAM and ROM) configured to process the acquired echoed ultrasound signals. Thus, the microcontroller of the probe is configured to execute the instructions of the software application recorded the embedded memory of the probe. Such a probe is then autonomous for the reconstruction of the ultrasound images, measurement of the echoed ultrasounds and notification of the measurements and/or the reconstruction to the operator.

Emitting Cone Selection

As detailed hereinbefore, a probe adapted for imaging measurements advantageously comprises an ultrasonic device configured for emitting ultrasound signals within at least two emitting cones and for receiving corresponding echoed ultrasound signals, the at least two emitting cones extending in different directions, as illustrated in FIGS. 1b, 1c, 3, 4, and 5.

However, in order to reduce power consumption and to improve the quality of the results by avoiding parasitic signals, it is advantageous to select the emitting cone(s) to be used.

FIG. 7 is a diagram illustrating an example of steps of a general method for scanning material according to particular embodiments of the invention.

As illustrated, the method comprises a step of receiving an item of information relating to a direction for emitting and receiving ultrasound signals (step 700).

According to some embodiments, the item of information corresponds to the direction along which a user and/or a system wishes the ultrasound signal to be emitted. It can be chosen for example, according to areas of interest in the patient's mouth. It may be expressed as an angle determined as a function of an angular position relative to a reference position of the probe. A spatial frame of reference may be used for example as a reference position of the probe.

According to other embodiments, the item of information corresponds to a desired emitting cone that may be expressed by a direction determined as a function of a reference position and by a cone angle (a solid angle).

Further, the method comprises a step of selecting one or several emitting cones of the probe as a function of the received item of information (step 705). According to some embodiments, a test may be carried out to check that the direction associated with the received item of information corresponds to emitting cones associated with the transducers of the probe 100. If no emitting cone corresponds to the direction associated with the received item of information, the process ends. Otherwise, one or more emitting cones are selected, based on the direction associated with the received item of information and, if needed, on a predetermined cone angle or a cone angle associated with the received item of information.

Next, the method comprises a step of energizing the ultrasound probe 100 to selectively emitting an ultrasound signal within the selected emitting cone(s) (step 710), i.e. according to the item of information. This step aims at controlling the probe 100 so that only the transducer(s) associated with the selected emitting cone(s) emit(s) an ultrasound signal. Thus, according to the intraoral structures that the operator wishes to observe or that should be controlled using protocols, the method makes it possible to easily select the transducer associated with the best emitting cone(s). Also, even though the areas of interest may be arranged in different areas of the mouth of a patient, the present method facilitates the commutation between the best positioned transducers for each area of interest.

According to some embodiments, the step of selecting may comprise selecting received echoed ultrasound signals. In this case, the ultrasound probe 100 emits with both emitting cones, and selectively receives the echoed ultrasounds signals. In other words, only received echoed signals detected by a (the) selected transducer(s) are processed.

According to some embodiments, the steps of selecting may comprise selecting the received ultrasound signals and selecting the ultrasound signals to be emitted as a function of the received item of information.

The step of the method of receiving an item of information relating to a direction for emitting an ultrasound signal may comprise other steps depending on selection criteria.

Hereinafter, details of the method are provided when the selection of the emitting cone(s) is manual, semi-automatic or automatic.

Manual Selection of the Emitting Cone

When the selection of the emitting cone(s) is manual, the step of receiving an item of information comprises receiving a user input.

When exploring the intraoral structure of a patient mouth, the user can provide an input to the probe regarding the position of the area of interest to be observed.

Once the user input is received, the item of information is determined. As explained hereinbefore, the item of information may be an angle determined as a function of a spatial reference frame associated with the probe or a desired emitting cone (that may be expressed as a direction determined as a function of a reference position and by a solid angle).

The determination of the item of information from the user input depends on the user input type and the configuration of the used probe.

According to some embodiments, the user input results from a predetermined mechanical pressure of the ultrasonic imaging probe 100 against an intraoral surface. In particular, the user input can result from a mechanical pressure of the probe 100 against an intraoral surface according to a direction in which the operator wants measurements to be done. For example, the direction can be a direction in which the area of interest is located or opposite to the area of interest.

According to some embodiments, a mechanical pressure may be detected for any angular position, with respect to the longitudinal axis, on an annular surface of the probe. Therefore, by associating mechanical pressure sensors with angular positions determined as a function of a reference frame associated with the probe and by defining a default value for a solid angle of an emitting cone, a desired emitting cone may be defined from a detected mechanical pressure. Typically, the default value for a solid angle of an emitting cone corresponds to the solid angle of the emitting cones of the transducers. According to some embodiments, the value of the solid angle can be changed by the user, for example depending on the mechanical pressure duration or through user preferences of an acquisition software interface.

When using a probe like those illustrated in FIGS. 3 and 4, the selected emitting cone(s) is(are) the one(s) associated with the transducer(s) closest to the desired emitting cone.

When using a probe like the one illustrated in FIG. 5, the desired emitting cone defines one or several angular positions of the transducer: the transducer emits ultrasound signals in the defined angular position(s) for which the mechanical pressure has been detected.

According to some embodiments, it is possible to limit the number of selected transducers (or emitting cones or emitting fan beams (that result in pseudo emitting cones when used)), by choosing the selected emitting cones (or emitting fan beams) that are the closest to the desired emitting cone. To this end, several solutions are possible, for example by choosing the emitting fan beam having the largest intersection area with the desired emitting cone. It is also possible to select the emitting fan beams having an intersection area with the desired cone that is greater than a predetermined threshold.

According to some embodiment, the pressure sensor comprises several elements, each element acting as an individual pressure sensor associated with a predetermined angular position in relation to the longitudinal axis of the probe. Each element may be associated with an emitting cone, such that once it detects a mechanical pressure, a corresponding emitting cone is directly selected.

For example, regarding a probe like the ones illustrated in FIGS. 3 and 4, each element may be arranged in proximity to a transducer so that detection of a mechanical pressure makes it possible to directly select one transducer.

Thereby, a user holding the probe 100 in his hand when exploring the intraoral structures of a patient can press the tip 115 of the probe 100 against the area of interest that he wants to observe. The direction of the mechanical pressure against the area of interest is then considered as a user input indicating the direction in which the ultrasound signal is to be emitted. The pressure is then converted into a signal configured to commute the transducer(s) associated with the selected emitting cone(s) to make it or them emit ultrasound signals in the desired cone. The operator can select other transducers when exploring other areas of interest of the patient's intraoral cavity. To this end, the operator applies a mechanical pressure against the next area of interest.

Naturally, the pressure sensor (and its elements) is able to detect a pressure with a predetermined force and/or with a predetermined duration.

According to some embodiments, the user input results from a predetermined motion of the ultrasonic imaging probe 100. Thus, any motion of the probe 100 is detected by a motion sensor and/or orientation sensor, embedded in the probe 100 and configured to detect predetermined command motions. Naturally the motion and/or orientation sensors are able to detect a movement with a predetermined velocity and/or duration, and/or a movement forming a geometrical shape.

The determination of the item of information in this embodiment may be carried out thanks to predetermined movements associated with angular positions according to a spatial reference frame associated with the probe, for example in relation to the longitudinal axis. In addition, the predetermined motions may be associated with predetermined values of solid angles of emitting cones.

Next, when a user performs a gesture, the movement is analyzed to determine if the gesture is similar to a predetermined movement. Therefore, by associating predetermined motions with angular positions determined as a function of a spatial reference frame associated with the probe and by defining a default value for a solid angle of an emitting cone, a desired emitting cone may be defined from a detected motion. Typically, the default value for a solid angle of an emitting cone corresponds to the solid angle of the emitting cones of the transducers.

When using a probe like those illustrated in FIGS. 3 and 4, the selected emitting cone(s) is(are) the one(s) associated with the transducer(s) closest to the desired emitting cone.

When using a probe like the one illustrated in FIG. 5, the desired emitting cone defines one or several angular positions of the transducer: the transducer emits ultrasound signals in the defined angular position(s) for which the motion has been detected. For example, an operator holding the probe 100 in his hand when exploring the intraoral structures of a patient can apply short and fast movement with the tip 115 of the probe 100. In particular, motions toward left or right may be considered as a user input indicating the direction in which measurements are to be made and thus, the direction in which an ultrasound signal is to be emitted.

According to some embodiments, the user input results from an actuation of a physical button arranged on the ultrasonic imaging probe 100. As described in relation with FIGS. 1a and 1b, each button 125-1, 125-2 can be configured to be linked to a transducer associated with an emitting cone.

Likewise, the user input can result from an interaction with a touch-sensitive screen of the probe or connected to the probe.

The item of information is determined differently according to the nature of the user input. In the case of a physical button, the buttons are programmed to be each associated with a transducer of the probe (or a position of a mobile transducer). Accordingly, when the user actuates a button, the item of information may correspond to the transducer to be activated.

In the case of the touch-sensitive screen, the user may indicate one or several angular positions and/or an angle, for example by drawing on a top display of the probe a circular sector indicating an emitting cone to be used. In such a case, the item of information may comprise, for example, one angular position and a solid angle or two angular positions, defining the desired emitting cone.

When using a probe like those illustrated in FIGS. 3 and 4, the selected emitting cone(s) is(are) the one(s) associated with the transducer(s) closest to the desired emitting cone.

When using a probe like the one illustrated in FIG. 5, the desired emitting cone defines one or several angular positions of the transducer: the transducer emits ultrasound signals in the defined angular position(s) between the two angular positions.

According to some embodiments, the user input results also from choosing of an item displayed on a software graphic interface hosted on a computer connected to the ultrasonic imaging probe 100. As illustrated in FIG. 6, the electronic system of the imaging probe 100 can be interfaced with a remote computer through an input/output interface. In this case, the computer hosts a program configured to operate the probe 100, and particularly to indicate in which direction the user wants to make measurements, as described hereinbefore for the touch screen.

The selection of the emitting cone as explained hereinbefore can result in the selection of more than one transducer (for a probe like those illustrated in FIGS. 3 and 4).

Semi-Automatic Selection of the Emitting Cone

According to some embodiments, the selection of the emitting cone(s) to be used is semi-automatic. An input relating to the direction for emitting an ultrasound signal is provided by a software hosted on the remote computer connected to the probe 100 (through an input/output interface).

The item of information is deduced from the input provided by the software. For example, the software, according to the area of interest to be observed in compliance with the protocol, provides one or several angular position(s), with respect to the longitudinal axis of the probe. Therefore, considering the angular position(s) and by defining a default value for a solid angle of the emitting cone, a desired emitting cone may be defined from a software input. Typically, the default value for a solid angle of an emitting cone corresponds to the solid angle of the emitting cones of the transducers.

As explained hereinabove, the ultrasound signals may have a cone or a fan beam shape. Consequently, the emitting cone or the emitting fan beam are selected differently.

According to some embodiments, when using a probe such as those illustrated in FIGS. 3 and 4, the selected emitting cones are the ones intersecting the desired emitting cone. According to a particular embodiment, it is possible to limit the number of selected cones by identifying the emitting cones that are arranged the closest to the desired emitting cone. To this end, several solutions are possible, for example by choosing the emitting cone having the largest intersection area with the desired cone defined by the item of information. It is also possible to select an emitting cone having an intersection area with the desired cone greater than a predetermined threshold.

According to some embodiments, ultrasound fan beams contained in the selected emitting cones may be selected/chosen.

According to some embodiments, the selected ultrasound fan beam may be chosen among the ones intersecting the desired emitting cone. To limit the number of selected ultrasound fan beams, the closest ultrasound fan beam is identified, for example by choosing the ultrasound fan beam having the largest intersection area with the desired cone defined by the item of information. It is also possible to select the emitting fan beam having an intersection area with the desired cone superior to a predetermined threshold.

When using a probe like the one illustrated in FIGS. 5*a* and 5*b*, the desired emitting cone makes it possible to determine the angular position(s) of the transducer in which an ultrasound signal is to be emitted.

An operator holding the probe 100 is then guided by the software through the acquisition process. The software can provide protocols ensuring the scan of a patient's intraoral cavity in the most efficient way, by limiting switching from one emitting cone to another. For example, pocket depth measurements can first be performed for left lingual mandibula, right vestibular mandibula, right lingual maxilla and left vestibular maxilla, and then the other dental arch areas using the other side of the probe in order to limit the number of times the system has to switch. Next, the scanning process is optimized and the amount of time to do a complete examination of a patient's intraoral cavity is reduced.

In this embodiment, the active transducer associated with the selected emitting cone may be indicated to the operator, for example with the help of LEDs on the probe 100 and/or on the acquisition interface of the remote computer.

Naturally, during the scanning, the operator can switch to the manual mode, and then manually select the direction in which the ultrasound signals are emitted, as described hereinbefore.

Automatic Selection of the Emitting Cone

According to particular embodiments, the selection of the emitting cone(s) to be used is automatic. For the sake of illustration, two examples of the steps of receiving an item of information relating to a direction for emitting an ultrasound signal are illustrated in FIGS. 8 and 9.

FIG. 8 illustrates a diagram of a first embodiment for automatic selection. This embodiment aims at performing an automatic detection of the presence of biological tissues in the direct environment of the probe 100 and thus selecting transducer(s) making it possible to carry out measurements on these biological tissues. In other words, this method enables detection of the direction in which an ultrasound signal is to be emitted in order to observe intraoral tissues (corresponding to the relative direction in which the biological tissues are arranged in relation to the probe 100). Next, the transducer(s), associated with the emitting cone(s) comprising said direction, is(are) activated automatically.

According to the illustrated example and in order to limit interference, the transducers may be energized one after another.

As illustrated, for receiving an item of information, the method comprises a step 800 of emitting an ultrasound signal within one of a plurality of emitting cones. To that end, the corresponding transducer is energized in order to emit an ultrasound signal in the associated emitting cone.

Directly after emitting the ultrasound signal, the method comprises a step 805 of measuring echoed ultrasound signals. Indeed, after emitting an ultrasound signal, the ultrasound signal is reflected and deviated by the surrounding tissues.

As illustrated, the previous steps (steps 800 and 805) are repeated for all (or several) of the transducers.

For determining the presence or not of biological tissues, the method comprises a step of comparing the measured echoed ultrasound signals with each other and/or comparing the measured echoed ultrasound signals with a threshold (step 810).

To determine whether the echoed ultrasound signals corresponds or not to ultrasound signals reflected by biological tissues, the energies of the measured echoed ultrasound signals are analyzed and compared to a threshold to determine whether these signals correspond to a detection of biological tissues or to noise.

Also, it is possible to compare all the measured echoed ultrasounds with each other in order to identify the ones with similar values that are greater than the others. For example, it is possible to select the measured echoed ultrasounds having a value approximately 90% of the maximum value of the measured echoed ultrasound signals.

Once the ultrasound signal threshold, corresponding to the presence of the tissues or desired material response, is established, the emitting cones associated with the measured echoed ultrasounds that are greater than the threshold, are selected.

FIG. 9 illustrates a diagram of a second embodiment for automatic selection of emitting cones. This embodiment aims at analyzing in real-time images built from the measured echoed signals after emitting ultrasound signals from several transducers of the probe 100 (or from several positions of a mobile transducer/mobile deflector). The selection of the emitting cone is made according to the features of the built images. The method is based on the fact that only the transducers that make it possible to provide meaningful images (or portions of images) should be selected.

For receiving an item of information, the method comprises a step of emitting an ultrasound signal within one of the emitting cones (step 900).

The echoed ultrasound signal is then measured (step 905) and the previous steps (steps 900 and 905) are repeated for all (or several) of the transducers.

Next, once the echoed ultrasound signals are measured by the transducers and images are built, the built images are analyzed (step 915), for example using standard feature analysis algorithms. This step aims at identifying the objects that are visible in the built images. In particular, the aim is to detect an intraoral structure within the images, indicating that the images are meaningful.

An area of interest (i.e. an area that the operator wants to observe) is characterized by a coupling agent thickness (for example a gel) followed with biological structures. Consequently, when these features are detected in a built image, the emitting cone(s) from which the ultrasound signals came from is (are) selected.

According to some embodiments, after receiving an item of information using one of the methods illustrated in FIGS. 8 and 9, one or several emitting cones can be selected. Indeed, it can occur that biological tissues are detected in more than one emitting cone from echoed ultrasound signals coming from ultrasound signals emitted in more than one emitting cone and/or from built images showing the area of interest.

If only one emitting cone is to be selected, the selection can be based on several criteria such as, for example, the built image quality or the proximity of the biological tissues.

According to some embodiments, the step of selecting one of the emitting cones comprises a step of selecting a subsector of one of the preselected cones as a function of the measured echoed ultrasound signals. For example, the subsector may be an ultrasound fan beam, or a cone comprised in one of the preselected cones or comprised in the desired cone. Indeed, the probe 100 can comprise subsectors in each emitting cone, associated with transducers, in order to monitor more precisely the direction in which ultrasound signals are sent.

The subsector of emitting cone is chosen as the one closest to the desired cone, meaning having the largest intersection area, while being included in the selected emitting cone.

According to some embodiments, the method comprises a step of energizing the indicator to indicate the selection of either received echoed ultrasound or ultrasound to be emitted according to the received item of information. Once the emitting cone is selected, an indicator, as one or several light emitting devices (LEDs), a display, arranged on the probe 100 as illustrated in FIGS. 1a and 1b, can be used to indicate to the operator which associated transducer is used. The operator is able to quickly have an indication regarding the direction according to which measurements are made.

Of course, with the help of physical buttons and/or on the graphical interface of the software operating the probe 100, it is possible for the operator to switch between the manual, semi-automatic and automatic modes.

When using a probe like the one illustrated in FIG. 5b, the automatic selection of an emitting cone or fan beam makes it possible to adapt the angle of the fan beam (or of the emitting cone) to the angular range in which the area of interest is positioned. Indeed, each angular position of either the rotating transducer (FIG. 5a) or the rotating deflector (FIG. 5b) is associated with an emitting cone. In that case, in the automatic selection, it is possible to identify a range of angular position of the rotating deflector or the rotating transducer between which biological tissues can be detected. Consequently, the emission angle of the ultrasound fan beam or cone is adaptive and can be sized according to the position of the biological tissues with coupling agent.

The invention claimed is:

1. A method for scanning material using a dental ultrasonic imaging probe comprising an ultrasonic device configured for emitting ultrasound signals from at least two ultrasound transducers having respective within at least two emitting cones for emitting and for receiving corresponding echoed ultrasound signals, the at least two ultrasound transducers and their respective emitting cones facing and extending in opposite and diverging directions with regard to a plane comprising the central longitudinal axis of a grip portion of the dental ultrasonic probe, the method comprising the steps of:
   receiving an item of information relating to a direction for emitting an ultrasound signal; and
   selecting received echoed ultrasound signals or ultrasound signals to be emitted, from at least one but less than all of said at least two emitting cones as a function of the received item of information.

2. The method according to claim 1, wherein receiving an item of information comprises:
   emitting an ultrasound signal in each of the at least two directions;
   measuring echoed ultrasound signals from each of the at least two directions;
   building images based on the measured echoed signals; and
   analyzing the built images;
and selecting comprises:
   controlling the ultrasonic imaging probe to selectively process echoed ultrasound signals or to selectively emit ultrasound signals in those of the at least two emitting cones in which biological structures are detected in the built images.

3. The method according to claim 1, wherein receiving an item of information comprises receiving a user input; and selecting comprises:
controlling the ultrasonic imaging probe to selectively process echoed ultrasound signals or to selectively emit ultrasound signals in one of the emitting cones closest to that indicated by the user input.

4. The method according to claim 3, wherein the user input results from a predetermined mechanical pressure of the dental ultrasonic imaging probe against an intraoral surface.

5. The method according to claim 3, wherein the user input results from an actuation of a physical button arranged on the dental ultrasonic imaging probe and/or from choosing an item displayed on a software graphic interface hosted on a computer connected to the dental ultrasonic imaging probe.

6. The method according to claim 3, wherein the user input results from a predetermined movement of the dental ultrasonic imaging probe.

7. The method according to claim 1, wherein the at least two emitting cones are obtained from two different transducers, from one moving transducer, or from a fixed transducer associated with a moving deflector.

8. A computer program for a programmable apparatus, the computer program comprising a sequence of instructions for implementing each of the steps of the method according to claim 1 when loaded into and executed by the programmable apparatus.

9. A device comprising a microprocessor configured for carrying out each of the steps of the method according to claim 1.

10. A method for scanning material using a dental ultrasonic imaging probe comprising an ultrasonic device configured for emitting ultrasound signals within at least two emitting cones and for receiving corresponding echoed ultrasound signals, the at least two emitting cones extending in opposite and diverging directions with regard to a plane comprising the central longitudinal axis of a grip portion of the dental ultrasonic probe, the method comprising the steps of:
receiving an item of information relating to a direction for emitting an ultrasound signal, wherein receiving an item of information comprises:
emitting an ultrasound signal in each of the at least two directions;
measuring respective echoed ultrasound signals from each of the at least two directions; and
comparing the respective measured echoed ultrasound signals with each other and/or comparing the respective measured echoed ultrasound signals with a threshold; and
selecting received echoed ultrasound signals or ultrasound signals to be emitted as a function of the received item of information, wherein selecting comprises:
controlling the ultrasonic imaging probe to selectively process echoed ultrasound signals or to selectively emit ultrasound signals in those of the at least two emitting cones that pass the function of the received item of information.

11. The method according to claim 10, wherein after receiving an item of information, the method further comprises a step of:
preselecting several fan beams or cones with different widths intersecting a respective one of the at least two emitting cones.

12. The method according to claim 11, wherein selecting one of the emitting ultrasound signals comprises:
selecting one of the preselected fan beams or cones, or selecting a subsector of one of the preselected fan beams or cones as a function of the measured echoed ultrasound signals.

13. A method for scanning material using a dental ultrasonic imaging probe comprising an ultrasonic device configured for emitting ultrasound signals within at least two emitting cones and for receiving corresponding echoed ultrasound signals, the at least two emitting cones extending in opposite and diverging directions with regard to a plane comprising the central longitudinal axis of a grip portion of the dental ultrasonic probe, and wherein the dental ultrasonic imaging probe comprises at least an indicator configured to provide an item of information relating to the selected emitting cone or a selected emitting direction, the method comprising the steps of:
receiving an item of information relating to a direction for emitting an ultrasound signal;
selecting received echoed ultrasound signals or ultrasound signals to be emitted as a function of the received item of information; and
energizing the indicator to indicate the selection.

14. The method according to claim 13, wherein the indicator comprises a plurality of light emitting devices.

* * * * *